United States Patent
Fann et al.

(10) Patent No.: US 11,760,777 B2
(45) Date of Patent: Sep. 19, 2023

(54) METHODS OF ANTIBODY PRODUCTION THAT MINIMIZE DISULFIDE BOND REDUCTION

(71) Applicant: BRISTOL-MYERS SQUIBB COMPANY, Princeton, NJ (US)

(72) Inventors: John C. Fann, Seattle, WA (US); Brian W. O'Mara, Seattle, WA (US); Laura R. Smith, Mercer Island, WA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 627 days.

(21) Appl. No.: 16/608,585

(22) PCT Filed: Apr. 24, 2018

(86) PCT No.: PCT/US2018/028998
§ 371 (c)(1),
(2) Date: Oct. 25, 2019

(87) PCT Pub. No.: WO2018/200430
PCT Pub. Date: Nov. 1, 2018

(65) Prior Publication Data
US 2020/0181193 A1 Jun. 11, 2020

Related U.S. Application Data

(60) Provisional application No. 62/490,410, filed on Apr. 26, 2017.

(51) Int. Cl.
*C07K 1/14* (2006.01)
*C07K 16/28* (2006.01)

(52) U.S. Cl.
CPC ............ *C07K 1/14* (2013.01); *C07K 16/2803* (2013.01)

(58) Field of Classification Search
CPC ...... C07K 1/14; C07K 16/2803; C07K 16/00; A61K 39/39591
See application file for complete search history.

(56) References Cited

U.S. PATENT DOCUMENTS 8,574,869 B2 * 11/2013 Kao .................... C07K 1/14
435/325
10,189,902 B2 * 1/2019 Maurer .............. C07K 16/2803

2009/0053786 A1 2/2009 Kao
2016/0176963 A1 6/2016 Maurer
2017/0002393 A1 1/2017 Singh
2017/0356022 A1* 12/2017 Khan .................... C12M 41/34

FOREIGN PATENT DOCUMENTS

WO WO2009009523 A2 1/2009
WO 2013075849 A1 5/2013

OTHER PUBLICATIONS

Liu et al., mAbs 2(5): 480-499 (Year: 2010).*
Cura et al., An End-to-End Approach to Monitoring and Reducing LMW Formation During mAbProcess Development, Presentation 251st American Chemical Society National Meeting and Exposition, 2016.
Handlogten et al., Glutathione and Thioredoxin Systems Contribute to Recombinant Monoclonal Antibody Interchain Disulfide Bond Reduction During Bioprocessing, 2017, 1469_1477, 114:7, Biotechnology Bioengineering.
John C. Fann, Challenges of Antibody Disulfide Bond Reduction in the Large-Scale Manufacturing Using Single-Use Technology, 2017, BPI Europe.
Mullan et al., Disulphide Bond Reduction of a Therapeautic Monoclonal Antibody During Cell Culture Manufacturing Operations, 2011, 1_3, 5:Supple 8: P110, BMC Proceedings.
Mun et al., Air Sparging for Prevention of Antibody Disulfide Bond Reduction in Harvested Cho Cell Culture Fluid, 2015, 734_742, 112, Biotechnology Bioengineering.
Trexler_Schmidt et al., Identification and Prevention of Antibody Disulfide Bond Reduction During Cell Culture Manufacturing, 2010, 452_461, 106:3, Biotechnology Bioengineering.
Chung, et al; Biotechnology and Bioengineering; "Effects of Antibody Disulfide Bond Reduction on Purification Process Performance and Final Drug Substance Stability"; pp. 1264-1274; vol. 114, No. 6.; Jun. 2017; First Published Online on Mar. 6, 2017.

* cited by examiner

*Primary Examiner* — Phuong Huynh
(74) *Attorney, Agent, or Firm* — Gregory R. Bellomy

(57) ABSTRACT

The present disclosure discloses methods for purifying antibodies providing an air overlay or headspace to single-use storage bags containing the antibody during purification. In specific embodiments, the application relates to purification of antibodies to human TIGIT (T cell immunoreceptor with Ig and ITIM domains), such as antibody 22G2, which decrease unwanted disulfide bond reduction. The application further provides depth filtration at lower throughput and/or flux, which also minimizes unwanted disulfide bond reduction.

13 Claims, 9 Drawing Sheets
Specification includes a Sequence Listing.

METHODS OF ANTIBODY PRODUCTION THAT MINIMIZE DISULFIDE BOND REDUCTION

CROSS-REFERENCE TO RELATED APPLICATIONS

The present application is a national stage of International Application Serial No. PCT/US2018/028998, filed Apr. 24, 2018, which claims priority to U.S. Provisional Application Ser. No. 62/490,410, filed Apr. 26, 2017.

FIELD OF THE INVENTION

The present application discloses methods of preparing therapeutic antibodies that avoid unwanted disulfide bond reduction.

BACKGROUND

Antibodies have become important therapeutic agents in treatment of many diseases, including inflammatory disorders and cancers. As large, complex polypeptide complexes, therapeutic antibodies present many challenges in production and purification. Degradation and chemical modifications (e.g.) can arise during purification that reduce potency of the antibody, increase its immunogenicity, alter bioavailability, and/or decrease its stability in storage. Such structural alterations include, e.g., deamidation (e.g. Asn to Asp, Gln to Glu), oxidation, reduction, clipping (e.g. clipping of C-terminal lysine), N-terminal pyro-glutamate formation, altered glycosylation, and aggregation. Structural alterations that paradoxically enhance biological activity are also problematic because the antibody no longer has the biological activity that it has when tested for safety and efficacy. Even structural alterations that are functionally inert may result in drug product heterogeneity, which is undesirable due to objections from regulatory agencies. Ideally a preparation of a therapeutic antibody will comprise a single species of antibody molecule, and multiple preparations of the same antibody will comprise this single species.

One such structural modification of therapeutic antibodies is disulfide bond reduction. Therapeutic antibodies typically comprise a complex of two heavy chains and two light chains. Two disulfide bonds hold the two heavy chains together, and one light chain is linked to each of the heavy chains by a disulfide bond. Reduction of any of these bonds may result in partial antibodies lacking one or more of the usual four polypeptide chains. The two antigen binding domains of antibodies, which provide target specificity, each comprise the amino terminal regions ("variable domains") of one heavy chain and one light chain, so dissociation of any chain will disrupt at least one antigen binding domain, resulting in reduced binding avidity, reduced valency and potentially less therapeutic efficacy.

Single-use technology is increasingly used in the production of therapeutic antibodies due to the ease of maintaining sterile conditions and sample processing. However, conditions for antibody production using single-use technology, including storage of partially purified antibodies are various steps in the purification process in bags, must be optimized to prevent degradation and chemical modification of antibodies. The need exists for improved methods of producing therapeutic antibodies using single-use technology that reduce or eliminate such degradation and chemical modification, including unwanted disulfide bond reduction.

SUMMARY OF THE INVENTION

The present invention provides improved methods of purifying antibodies, including antibodies to human TIGIT, such as mAb 22G2, in which an air overlay or headspace is provided when partially purified antibody is stored in disposable plastic bags between steps in the purification.

In some embodiments, the method of the present invention involves maintaining or introducing an air overlay over a partially purified antibody preparation, such as a clarified bulk sample after depth filtration, for example in a disposable clarified harvest bag. In some embodiments, the percentage of intact mAb in the antibody that is stored under the air overlay does not drop below 90%, or below 95%, at any point during storage.

In various embodiments the specified percent volume of the air overlay or headspace is between 5 and 50%, such as between 10 and 30%, for example between 15 and 25%, and in specific embodiments, is approximately 20%, or is 20%. In one embodiment, the partially purified antibody is stored in between depth filtration and protein A chromatography, e.g. for 8, 12 or 16 hours, or for 1, 2, 3, 4, 5, 6, 7 or more days. In some embodiments the partially purified antibody preparation is agitated while it is stored under an air overlay or headspace of the invention, such as agitation using an impeller inside the storage vessel (e.g. a bag). In some embodiments the air overlay or headspace is refreshed during storage, e.g. with clean compressed air, either intermittently, substantially continuously or continuously for the duration of storage.

In some embodiments, the antibody being purified is an anti-human TIGIT mAb, such as mAb 22G2, including isotype variants thereof, including mAb 22G2 IgG1.1f. In some embodiments, the antibody being purified comprises CDRH1, CDRH2 and CDRH3 of SEQ ID NOs: 20, 21 and 22, respectively, and CDRL1, CDRL2 and CDRL3 of SEQ ID NOs: 23, 24 and 25, respectively. In further embodiments, the antibody being purified comprises a heavy chain variable domain sequence of SEQ ID NO: 7 or 8, and a light chain variable domain sequence of SEQ ID NO: 9, for example a heavy chain comprising SEQ ID NOs: 7 and 48, and a light chain comprising SEQ ID NOs: 9 and 49.

In another aspect, the methods of purifying an antibody of the invention involve depth filtration at low throughput to minimize disulfide bond reduction, such as a throughput of less than or equal to 80 L/m², less than or equal to 70 L/m², or less than or equal to 60 L/m². In another embodiment, the methods of purifying an antibody of the invention involve depth filtration at low flux, such as less than or equal to 50 LMH (L/m²/h), or less than or equal to 25 LMH.

Other features and advantages of the instant disclosure will be apparent from the following detailed description and examples, which should not be construed as limiting.

BRIEF DESCRIPTION OF THE DRAWINGS

FIG. 4A shows a rapid build-up of pressure at throughputs of over approximately 50 L/m² for depth filter type 30SP02A (solid line). FIGS. 4B and 4C show that LDH and thiol content both increase at higher throughput. Increased LDH is indicative of increased cell lysis, and increased thiol content indicates a more reducing environment.

DETAILED DESCRIPTION

Figure 1:
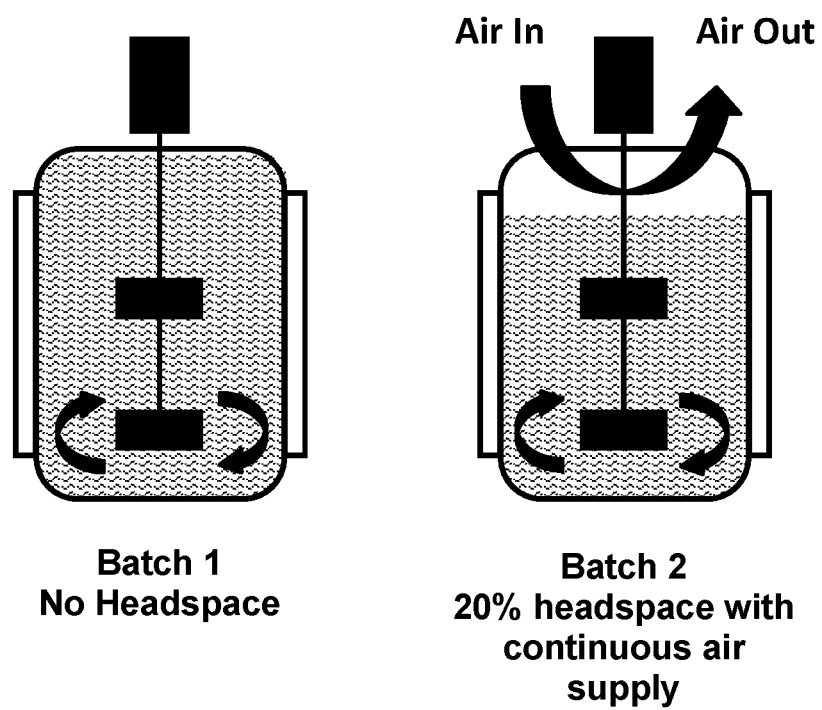
FIG. 1 is a schematic representation of the invention that compares a "Batch 1" process with no air headspace in the antibody preparation storage vessel and a "Batch 2" process with a 20% air headspace (scale is approximate). The rounded rectangle represents the containment vessel, e.g. a disposable bag. The black rectangles inside the vessel represent the blades of the optional impeller, which may provide agitation (represented by curved ribbons), either intermittently or semi-continuously or continuously during storage, with the black rectangle outside the vessel representing the agitation mechanism (motor). The "Air In"/"Air Out" ribbon represents optional fresh air flow during storage, which may be intermittent, semi-continuous or continuous during storage.

Antibodies to TIGIT are in clinical development, as monotherapy and in combination with PD-1/PD-L1 inhibitors, for immunotherapy of cancer. Accordingly, there is a need for improved methods for producing such antibodies. Preferably such methods are not subject to unwanted disulfide bond reduction during the purification process.

The present invention provides such improved methods for large scale production of therapeutic monoclonal antibodies using single-use technology. The methods comprise maintaining or introducing an air overlay or headspace, e.g. an air overlay, in disposable storage bags when an antibody preparation is to be stored, e.g. for one or more days, prior to further purification. The present invention further provides depth filtration at lower throughput, which also helps minimize unwanted disulfide bond reduction.

Definitions

In order that the present description may be more readily understood, certain terms are first defined. Additional definitions are set forth throughout the detailed description.

TIGIT refers to "T cell immunoreceptor with Ig and ITIM domains," a member of the PVR (poliovirus receptor) family of immunoglobin proteins, which binds to PVR/CD155 and Nectin-2/CD112. TIGIT is also referred to as TIGIT, WUCAM, Vstm3 and Vsig9. Unless otherwise indicated, or clear from the context, references to TIGIT herein refer to human TIGIT ("huTIGIT"), and anti-TIGIT antibodies refer to anti-human TIGIT antibodies (anti-huTIGIT antibodies). Human TIGIT is further described at GENE ID NO: 201633 and MIM (Mendelian Inheritance in Man): 612859. The sequence of human TIGIT (NP_776160.2), including 21 amino acid signal sequence, is provided at SEQ ID NO: 1. Unless otherwise indicated, or clear from the context, "inhibition" of TIGIT refers to blocking of PVR binding and signaling. Anti-TIGIT antibodies of the present invention may act by inhibition of TIGIT signaling, blockade of TIGIT/DNAM-1 interaction and/or other mechanisms, such as directing the depletion of regulatory T cells.

PVR (poliovirus receptor) interacts with TIGIT to induce an immunosuppressive signal. PVR is also referred to as PVS; HVED; CD155; NECL5; TAGE4; Necl-5. Unless otherwise indicated, or clear from the context, references to PVR/CD155 herein refer to human PVR ("huPVR"). Human PVR is further described at GENE ID NO: 5817 and MIM: 173850. There are four known human PVR transcript variants: alpha (NP_006496.4), beta (NP_001129240.1), gamma (NP_001129241.1) and delta (NP_001129242.2), the sequences of which are provided at SEQ ID NOs: 50-53. Unless otherwise indicated, reference to PVR or human PVR relates to the alpha transcript polypeptide.

Unless otherwise indicated or clear from the context, the term "antibody" as used to herein may include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies may exhibit modifications at the N- and/or C-terminal amino acid residues. For example, antibodies of the present invention may be produced from a construct encoding a C-terminal lysine residue, for example on the heavy chain, but such C-terminal lysine may be partially or totally absent in the therapeutic antibody that is sold or administered. Alternatively, an antibody may be produced from constructs that specifically do not encode a C-terminal lysine residue even though such lysine was present in the parental antibody from which the therapeutic antibody was derived. In another example, an N-terminal glutamine or glutamic acid residue in an antibody of the present invention may be partially or fully converted to pyro-glutamic acid in the therapeutic antibody that is sold or administered. Any form of glutamine or glutamic acid present at the N-terminus of an antibody chain, including pyro-glutamic acid, is encompassed within the term "glutamine" as used herein. Accordingly, antibody chain sequences provided herein having N-terminal glutamine or glutamic acid residue encompass antibody chains regardless of the level of pyro-glutamic acid formation.

Unless otherwise indicated, an "intact" antibody, or "intact mAb," refers to an antibody comprising two heavy chains and two light chains (HHLL), bound together by the usual pair of disulfide bonds that link the heavy chains to each other, and the single disulfide bonds that link each light chain to a respective heavy chain. The percentage of "intact mAbs" is calculated as the number of HHLL species present divided by the number of HHLL species that would be formed if all heavy and light chains were present in HHLL species (rather than in alternative species, such as H, L, HH, HL ("halfmer"), HHL), multiplied by 100. Species lacking one or more antibody chains are referred to herein as "low molecular weight" (LMW) species. The percentage of intact mAb may be measured by any suitable method, but unless otherwise indicated "intact mAb" is measured by Caliper LabChip® microfluidic analysis or a method based on the same principle (microfluidic capillary electrophoresis).

The term "monoclonal antibody," or "mAb," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. Human antibodies of the present invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody, e.g. a mouse antibody, are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody. A "hybrid" antibody refers to an antibody having heavy and light chains of different types, such as a mouse (parental) heavy chain and a humanized light chain, or vice versa.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in one or a few amino acids. See, e.g., Jefferis et al. (2009) mAbs 1:1.

The phrases "an antibody recognizing an antigen" and "an antibody specific for an antigen" are used interchangeably herein with the term "an antibody that binds specifically to an antigen."

An "isolated antibody," as used herein, refers to an antibody that is substantially free of other antibodies having different antigenic specificities (e.g., an isolated antibody that specifically binds to TIGIT is substantially free of antibodies that specifically bind antigens other than TIGIT). An isolated antibody that specifically binds to an epitope of human TIGIT may, however, have cross-reactivity to other TIGIT proteins from different species.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises CH2 and CH3 constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or an amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, MD; see also FIGS. 3c-3f of U.S. Pat. App. Pub. No. 2008/0248028. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG (including a C-terminal lysine). As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

Unless otherwise indicated, or clear from the context, amino acid residue numbering in the Fc region of an antibody is according to the EU numbering convention, except when specifically referring to residues in a sequence in the Sequence Listing, in which case numbering is necessarily consecutive. For example, literature references regarding the effects of amino acid substitutions in the Fc region will typically use EU numbering, which allows for reference to any given residue in the Fc region of an antibody by the same number regardless of the length of the variable domain to which is it attached. In rare cases it may be necessary to refer to the document being referenced to confirm the precise Fc residue being referred to.

The term "epitope" or "antigenic determinant" refers to a site on an antigen (e.g., TIGIT) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation.

As used herein, the specified percent volume of an air overlay or headspace above a sample is calculated by dividing the volume of air in the storage bag by the total interior volume of the bag when filled with the overlay/headspace and the antibody sample. The total interior volume is the sum of the volume of the overlay/headspace and the volume of the antibody solution in the bag.

The terms "overlay" and "headspace" are used herein to refer to a volume of air contained in a vessel, such as a bag, along with an antibody solution, such as CB. As used herein, an air "overlay" is a volume of air above a solution of antibody, which volume of air that is refreshed over time with new air, for example through inlet and outlet ports in the bag. This is as opposed to an air "headspace," which comprises a single bolus of air sealed in the bag, which is not refreshed. Typically, the benchtop scale experiments used to generate the data provided herein (e.g. at FIGS. 4-6) employ static headspaces, but larger scale GMP production (e.g. at FIG. 3) uses an air overlay.

The air overlay, or headspace, will typically be large enough to provide adequate oxygen to the CB to prevent disulfide bond reduction, and yet not so large as to unduly waste the capacity of the bag to store CB. The desired size of the overlay or headspace, when expressed as a percentage of the final total volume of the bag, is referred to as the specified percent volume. In various embodiments, the specified percent volume will be between 5 and 50%, or 10 and 30%, for example between 15 and 25%, and in specific embodiments approximately 20%, or 20%. "Approximately," in this context, means a value within usual experimental error range in the art for the recited value, e.g. a specified percent volume of approximately 20% refers to the value that might be obtained by a scientist or technician, using reasonable care, trying to achieve 20%.

As used herein, "maintaining" a specified percent volume of air headspace or headspace above a sample refers to partially filling a bag with a liquid sample to the point where the overlay/headspace, once the bag is closed, will be equal to the specified percent volume. Typically a disposable bag for storage of an antibody sample, e.g. clarified bulk (CB) antibody, will be filled with air before CB is added. Liquid CB will be added to the bag but filling will be stopped once the volume of liquid CB is (100%—specified percent volume). Alternatively, "introducing" a specified percent volume of air overlay or headspace above a sample refers to increasing the volume of air in a bag to reach the specified percent volume of overlay/headspace, e.g. by the addition of air to the bag. Such "introducing" can range from a small fraction of the headspace/overlay volume to the introduction of the entire volume of the headspace/overlay, i.e. in a bag initially devoid of any headspace/overlay. An air overlay or headspace is "maintained" in situations where the bag initially contains more air than the desired final headspace/overlay, and it is "introduced" when the bag initially contains less air that the desired final headspace/overlay.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

Various aspects described herein are described in further detail in the following subsections.

Methods of the Present Invention

Upstream processing for production of a therapeutic monoclonal antibody using single-use technology starts with a master cell bank comprising cells, often Chinese Hamster Ovary (CHO) cells, that express the antibody. In one embodiment, a cell culture is started in growth medium in a disposable flask, followed by growth in a WAVE Bioreactor. The culture is than passaged through a 200 L seed single-use bioreactor (SUB), a 500 L SUB, and ultimately a 2000 L production SUB in chemically defined media. The 2000 L culture is cultured for 14 days, or approximately 7 days beyond when it reaches maximum viable cell density (e.g. up to 26 million cells/ml), by which point cell viability drops to approximately 80%. The culture is then subjected to depth filtration to remove cells and cellular debris.

Depth filtration is performed under conditions to minimize the formation of low molecular weight (LMW) species arising from disulfide bond reduction, such as maintaining 40% dissolved oxygen, keeping the culture chilled at less than 10° C., and using a slow pump rate to avoid shear. See Cura et al. (17 Mar. 2016) $251^{st}$ Amer. Chem. Soc. Meeting, San Diego, California, Presentation 545 ("End-to-end approach to monitoring and reducing LMW Formation during mAb process development"). A titre of 2 g/l may be obtained.

The resulting clarified bulk (CB) solution of antibody is collected, and optionally stored, in a disposable clarified harvest bag. The CB is then run over a protein A column to collect antibody over the course of four one-day "cycles," with one quarter of the CB purified each day. Because it takes four days to complete the Protein A step, portions of the CB are stored for one, two and three days in the disposable clarified harvest bag prior to the protein A step. As used herein, "CB Cycle 1" refers to CB that is subjected to protein A chromatography the same day it is filtered, "CB Cycle 2" refers to CB that is subjected to protein A chromatography the day after (i.e. the sample that is stored for one day), "CB Cycle 3" refers to CB that is stored for two days, and "CB Cycle 4" refers to CB that is stored for three days. Due to the practicalities of the business work day, the term "day" as used in the context of storage of a CB sample need not be precisely 24 hours. The CB Cycle 2 samples that are processed "the day after" the CB Cycle 1 samples may actually be stored for less than 24 hours, such as at least 8, 12 or 16 hours, since "overnight" storage may entail starting protein A chromatography of CB Cycle 2 earlier in the day than CB Cycle 1, which necessarily took place after depth filtration on the previous day. As a consequence, CB Cycles 3 and 4 may also be stored for correspondingly less than 48 and 72 hours, but typically not less than 36 hours and 60 hours, respectively.

Downstream processing after protein A chromatography includes viral inactivation (VI) of CB, followed by cation exchange (CEX) chromatography, passage through an anion exchange (AEX) membrane, further viral inactivation, ultrafiltration/diafiltration by tangential flow filtration (TFF) and bottling. The material obtained after the first viral inactivation step is referred to as either "post viral inactivation" (post-VI) or "post-protein A/viral inactivation bulk" (PAVIB).

Figure 2A:
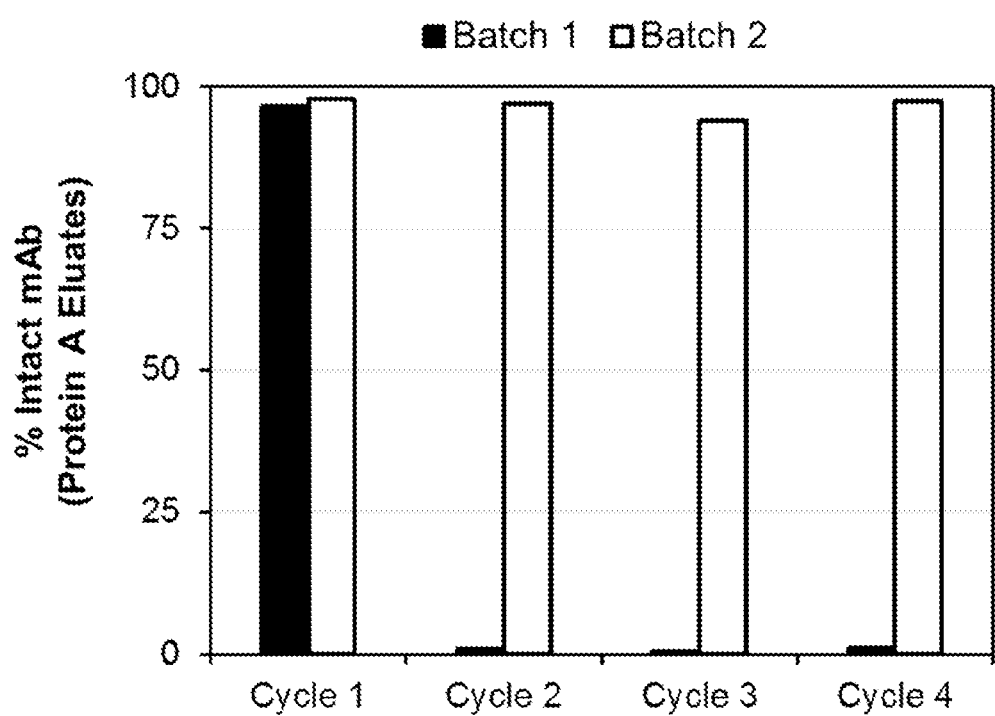
FIG. 2A shows the percentage of intact antibody at the Protein A Eluate stage of purification when prepared by convention methods (Batch 1, solid bars) and a method of the present invention (Batch 2, open bars). Data are presented for Cycles 1, 2, 3 and 4, which (as discussed in greater detail infra) represent samples run on the protein A column immediately after (i.e. the same day as) depth filtration (Cycle 1), run the next day (Cycle 2), etc. As is clear, samples stored overnight or longer by conventional methods (Batch 1) lose nearly all intact antibody whereas samples stored by the methods of the present invention (Batch 2) do not.
Figure 2B:
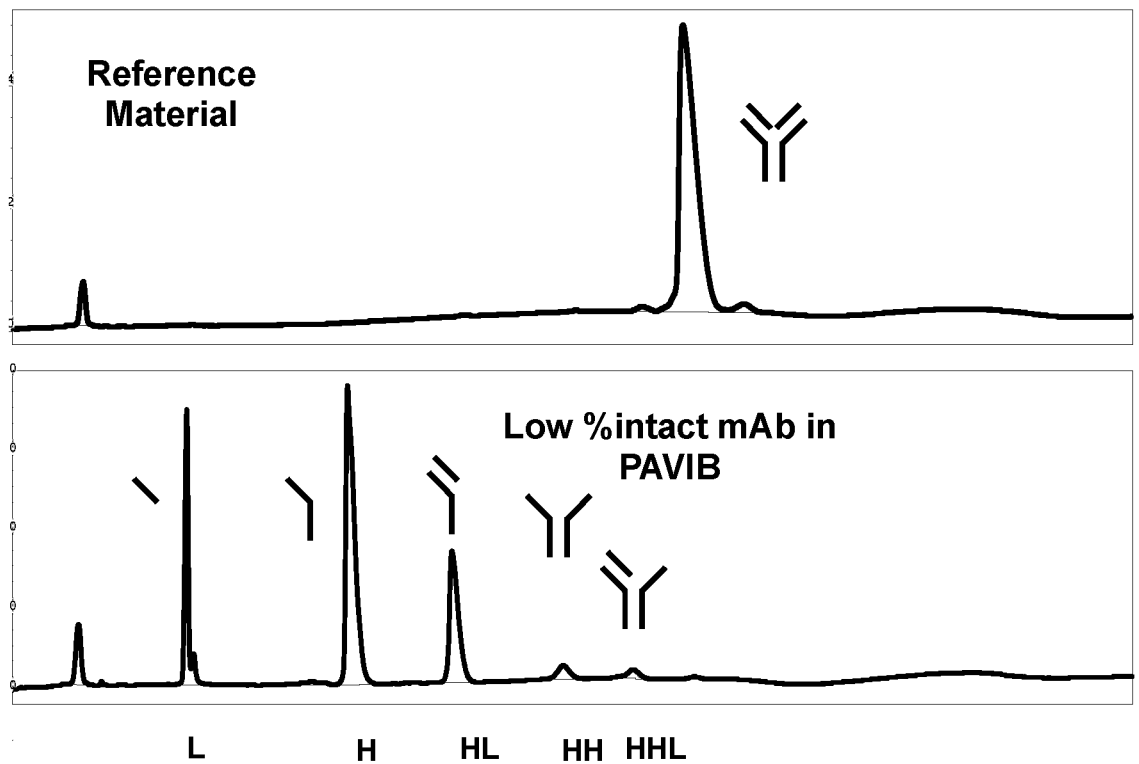
FIG. 2B provides the results of non-reducing SDS capillary electrophoresis of a reference material comprising intact mAb (upper panel), and a sample of antibody preparation after protein A chromatography and viral inactivation (PAVIB), also referred to as post-VI (discussed infra), that had been stored one or more days without an air overlay or headspace (lower panel). Graphical representations of antibodies illustrate the molecular species represented by the adjacent peak. Species are, from left to right, light chain (L), heavy chain (H), light/heavy chain complex (HL), dual heavy chain complex (HH), mAb lacking one light chain (HHL), and fully intact mAb. See Example 1. The vast majority of antibody in the PAVIB sample is present in antibody fragments. Unless otherwise indicated, all experimental results provided herein involve mAb BMS-986207, which is disclosed as mAb 22G2 in Int'l Pat. Pub. No. WO 2016/106302. The heavy chain of this mAb comprises SEQ ID NOs: 7 and 48, and the light chain comprises SEQ ID NOs: 9 and 49.
Figure 3:
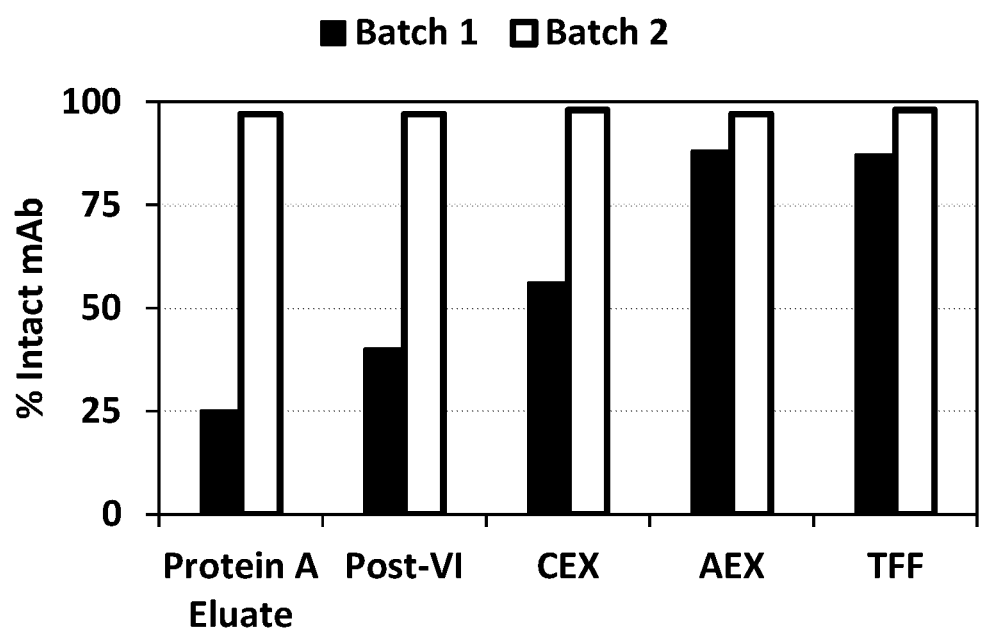
FIG. 3 shows the percentage of intact mAb at various stages of purification, i.e. after protein A chromatography (Protein A Eluate), post viral inactivation (post-VI), after cation exchange (CEX), after anion exchange (AEX), and drug substance obtained after tangential flow filtration (TFF). Data are provided for samples purified in the conventional manner ("Batch 1," also referred to as GMP #1, solid bars), in which portions of the antibody were stored one or more days in a disposable bag prior to protein A chromatography without an air overlay or headspace, and for clarified bulk (CB) samples stored according to the methods of the present invention ("Batch 2," also referred to as GMP #2, open bars), including use of an air overlay. See Examples 2 and 3. Only 25% of antibody is intact in samples stored in the conventional manner at the protein A eluate stage. (It is worth noting that the "25% intact antibody" value for the Batch 1 Protein A Eluate in FIG. 3 is a result of combining all of CB Cycles 1, 2, 3 and 4 (as discussed infra), where CB Cycle 1 had nearly 100% intact antibody but later CB Cycles comprised little to no intact antibody.) Although the percentage of intact mAb in the conventional preparation recovers during purification, it plateaus at 88%. In contrast, the percentage of intact mAb remains consistently above 95% for samples stored according to the methods of the present invention, including use of an air overlay.
Figure 4A:
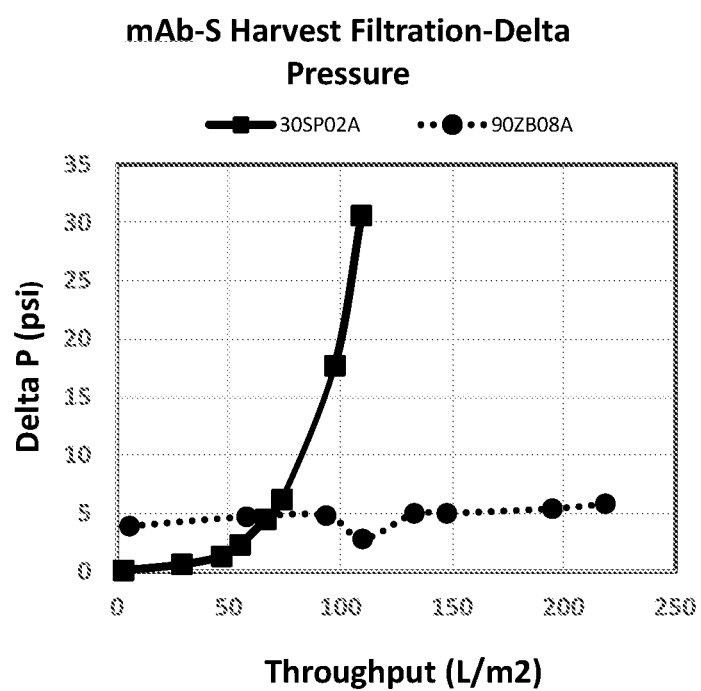
FIGS. 4A, 4B and 4C show the effect of throughput on pressure, lactate dehydrogenase (LDH) content and thiol content, respectively, in an antibody preparation subjected to depth filtration. See Example 5.
Figure 4B:
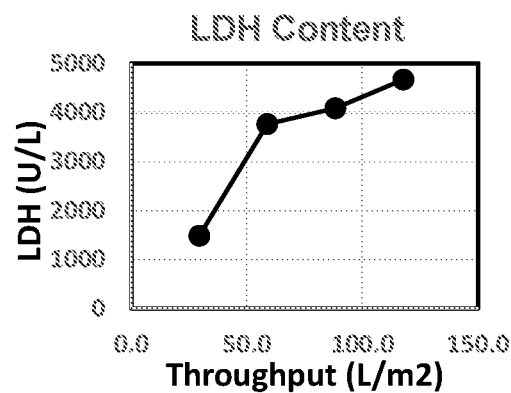
Figure 4C:
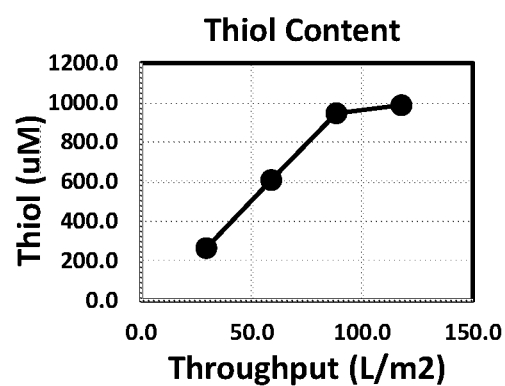

In one antibody preparation, GMP #1, PAVIB from CB Cycle 1 was >97% intact mAb, but all other PAVIB samples (from CB Cycles 2-4) were <15% intact, as determined by Caliper LabChip® microfluidic analysis (as described in Example 2). See FIG. 2A (Batch 1). The overall pooled preparation was 40% intact mAb (FIG. 3, Post-VI, left column). It is apparent from these results that serious unwanted disulfide bond reduction was taking place for samples stored overnight or for one or more days in clarified harvest bags between depth filtration and Protein A chromatography. FIG. 2B provides a chromatogram of a reference antibody preparation comprising intact mAb (upper panel) and a PAVIB sample from CB Cycle 2 (lower panel), showing the severe loss of intact mAb caused by reduction of disulfide bonds, with essentially no intact mAb remaining. Although antibody activity is not necessarily impaired, reduction of the drug substance (DS) has negative impacts on product compatibility and process consistency.

Although unwanted disulfide bond reduction occurs upon storage in the disposable clarified harvest bag, the percentage of intact mAb recovers over the course of the remaining purification steps. See FIG. 3. Nevertheless, the percentage of intact mAb never gets above 88%. Id.

In contrast, antibodies purified by the methods of the present invention (GMP #2), involving providing an air overlay (or headspace) above the antibody during storage in disposable bags prior to protein A purification, do not experience this unwanted reduction. See FIGS. 2A and 3 (Batch 2), Example 3. In fact, percent intact mAb remains at or above 97% at all downstream steps when purified by a method of the present invention. Id.

Bench studies confirm that low percent dissolved oxygen is responsible for unwanted disulfide bond reduction, and thus loss of intact mAb. Experiments are described at Example 4. Results are provided at Table 1. Samples that were stored for 0, 1, 2, or 3 days without aeration exhibit greatly reduced DO and reduced intact mAb. But parallel samples that were subsequently aerated to 100% DO (as indicated) maintained over 90% intact mAb, as shown in Table 1.

TABLE 1

Effect of Dissolved Oxygen (DO) and Aeration on DS Reduction

| Days w/o aeration | % DO | % Intact mAb | % DO post-aeration | % Intact mAb post-aeration |
|---|---|---|---|---|
| 0 | 100 | 97.6 | 100 | 96.8 |
| 1 | 51 | 97.4 | 100 | 96.6 |
| 2 | 4 | 1.1 | 100 | 92.2 |
| 3 | 4 | 1.4 | 100 | 92.1 |

The results from these bench studies are consistent with the large scale antibody purification results, and confirm that aeration to maintain high dissolved oxygen prevents unwanted disulfide bond reduction.

Surprisingly, simply providing an air overlay in the disposable storage bags, along with agitation during storage, provides aeration sufficient to prevent disulfide bond reduction. Prior art methods of maintaining high dissolved oxygen during antibody purification suggest sparging the samples with air or oxygen, for example in metal tanks. Mun et al. (2014) Biotechnol. Bioeng. 112:734; U.S. Pat. No. 8,574, 869. Sparging in disposable bags requires more sophisticated design at higher manufacturing cost, so it is not usually feasible for disposable CB bags. Sparging can also cause higher foaming inside the bag or cause over-oxidation of antibody products.

It was also found that the sample throughput during depth filtration effected the percent intact mAb. Filtration at throughputs of 59 L/m$^2$ or less showed no enhancement of disulfide bond reduction, whereas 88 and 118 L/m$^2$ reduced intact mAb to less than 40%. Without intending to be limited by theory, it is possible that shear forces at higher throughput and/or high flux cause cellular disruption and release of factors and enzymes that catalyze the disulfide bond reduction. Mun et al. (2014) Biotechnol. Bioeng. 112:734. As a consequence, the present invention provides for depth filtration of antibodies at throughputs of less than about 88 L/m$^2$, such as less than or equal to 80 L/m$^2$, less than or equal to 75 L/m$^2$, less than or equal to 70 L/m$^2$, or less than or equal to 60 L/m$^2$ to minimize unwanted disulfide bond reduction. The present invention also provides for depth filtration of antibodies at flux of less than about 50 LMH, such as less than or equal to 25 LMH, to minimize unwanted disulfide bond reduction.

Figure 6:
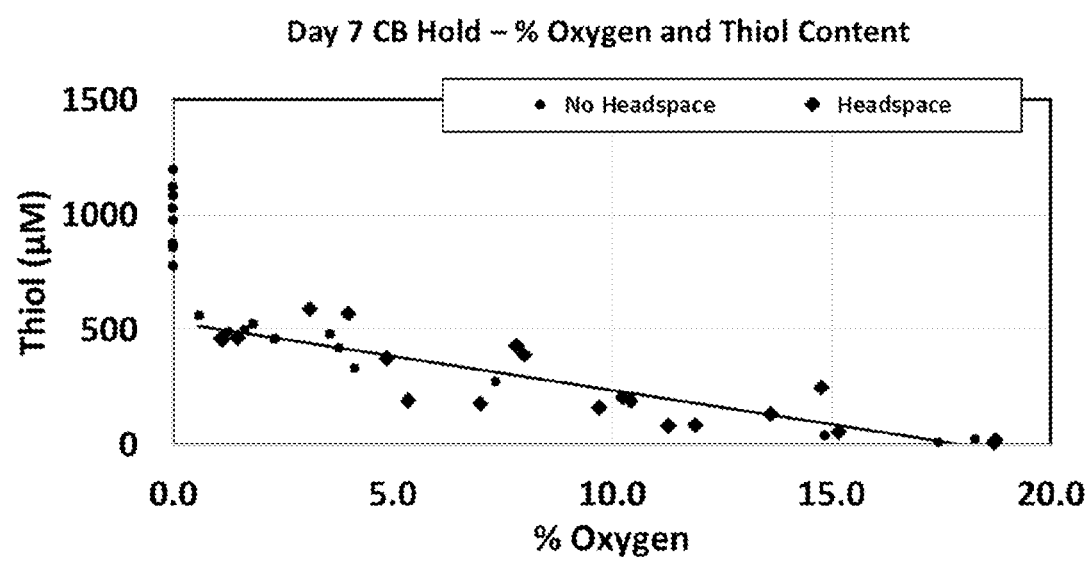
FIG. 6 shows thiol content as a function of dissolved oxygen for CB samples stored for 7 days with no headspace in a capped syringe, and similar samples stored with a headspace. See Example 6. Lower thiol levels correlated with increased oxygen, with essentially no thiol remaining at percent oxygen levels above 15-20%. Samples lacking a headspace typically exhibit much lower percent oxygen compared with those having a headspace. Many of the non-headspace samples had no detectable oxygen and elevated thiol content.
Figure 7A:
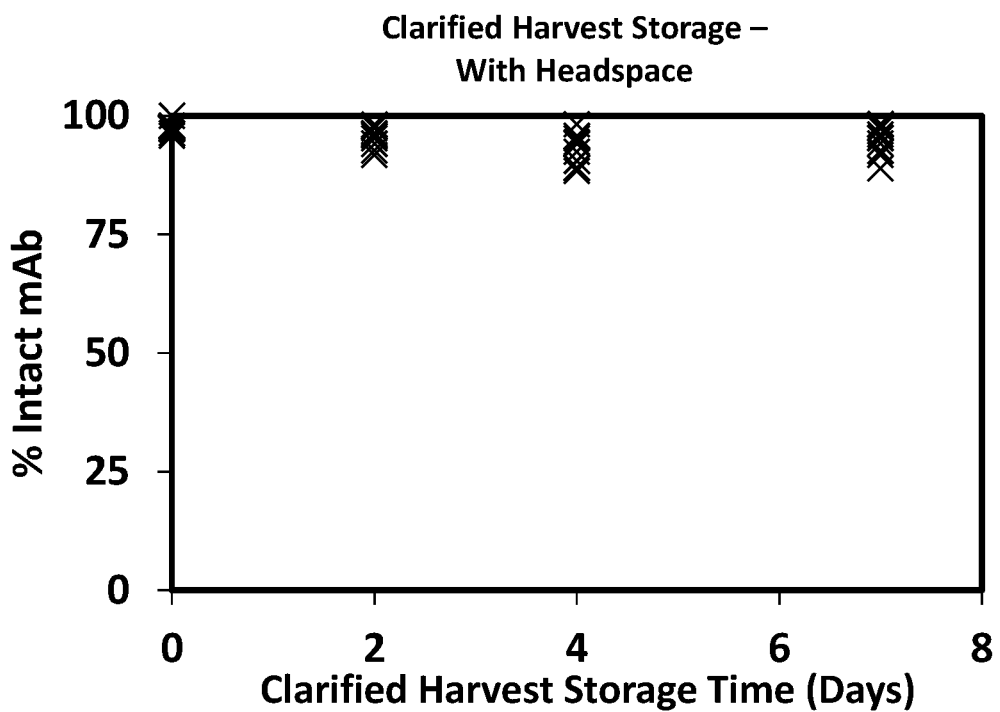
FIGS. 7A and 7B show the percentage of intact antibody in clarified harvest preparations stored at 4° C. for up to 7 days, either with (FIG. 7A) or without (FIG. 7B) a headspace. Data points represent percentage of intact antibody in samples depth filtered using different filters (30SP02A or 10SP02A) and at different flux (25, 50 or 75 LMH). Many of the samples stored without headspace (FIG. 7B), particularly those obtained with a smaller pore filter (30SP02A) and at high flux (50 or 75 LMH), show drastic reductions of intact antibody starting at least as early as 2 days of storage, whereas all samples stored with a headspace (FIG. 7A) maintain high levels of intact antibody over at least seven days regardless of filtration conditions.
Figure 7B:
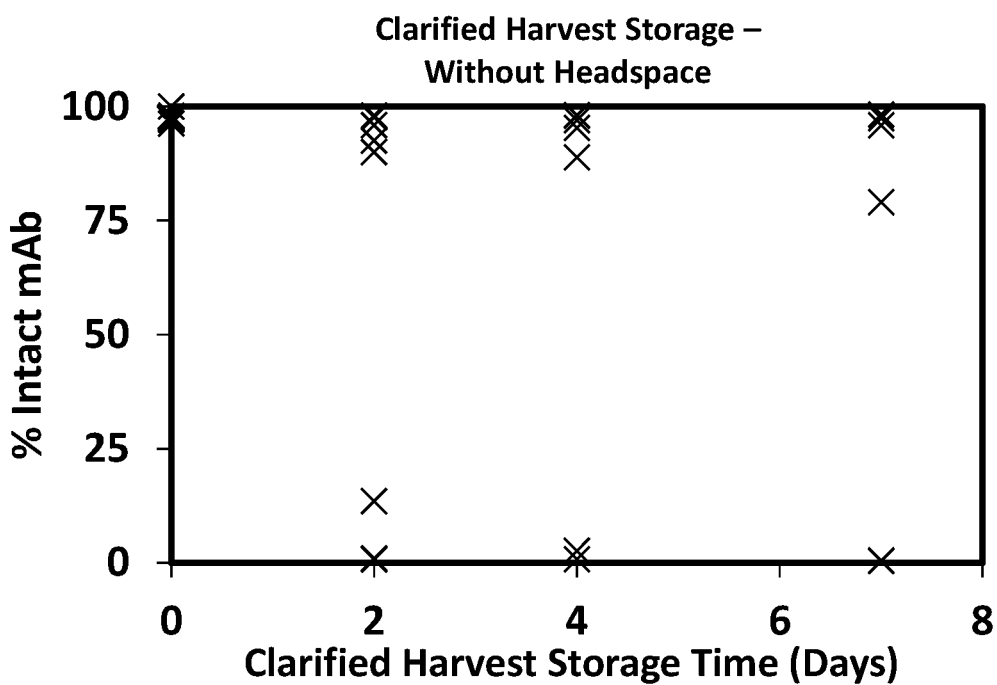

Further experiments confirmed that samples with an air headspace typically exhibit higher oxygenation and lower thiol content, consistent with the decreased level of disulfide bond reduction observed in antibody preparations. Results are provided at FIG. 6. See Example 6. Still further experiments show that antibodies prepared at high throughput and/or high flux are susceptible to severe loss of intact antibody upon storage for only a couple of days at 4° C. (FIG. 7B), but that the methods of the present invention prevent such unwanted reduction (FIG. 7A).

TIGIT—T Cell Immunoreceptor with Ig and ITIM Domains

The methods of the present invention find particular utility with anti-huTIGIT mAbs, such as mAb 22G2, including isotype variants thereof, including mAb 22G2 IgG1.1f (heavy chain comprising SEQ ID NOs: 7 and 48, and light chain comprising SEQ ID NOs: 9 and 49). Antibody 22G2 has a hydrophobic antigen binding domain, and has a high "spacial-aggregation-propensity" (SAP) score according to the model of Chennamesetty et al. (2010) J. Phys. Chem. B 114:6614. Other antibodies sharing this property may be particularly well suited to purification by the methods of the current invention.

TIGIT (T cell immunoreceptor with Ig and ITIM domains) is a co-inhibitory receptor protein also known as WUCAM, Vstm3 or Vsig9. TIGIT was discovered in genomic searches for proteins specifically expressed on T cells, and has an immunoglobulin variable domain, a transmembrane domain, and an immunoreceptor tyrosine-based inhibitory motif (ITIM), and contains signature sequence elements of the PVR protein family. It is known to interact with poliovirus receptor (PVR; CD155) and with nectin2 (CD112). See e.g. Stengel et al. (2012) Proc. Nat'l Acad. Sci. (USA) 19:5399; WO 2006/124667; WO 2009/126688. Although PVR may interact with the co-activating receptor DNAM-1 (CD226) to enhance tumor killing, the high affinity TIGIT/PVR interaction would inhibit such killing, and may act to prevent killing of normal (self) cells that also express PVR. Stanietsky et al. (2009) Proc. Nat'l Acad. Sci. (USA) 106:17858. The dominance of this inhibitory interaction may be important in suppression of anti-self immune reactions, but in the tumor context it suppresses tumor eradication. Id.

TIGIT suppresses T cell activation by promoting the generation of mature immunoregulatory dendritic cells. Yu et al. (2009) Nat. Immunol. 10:48. TIGIT and other such co-inhibitory molecules (e.g. CTLA-4, PD-1, Lag3 and BTLA) may play a role in evasion of immunosurveillance by tumor cells. Experiments have shown that PVR/CD155 is over-expressed on melanoma cells (Inozume et al. (2014) J. Invest. Dermatol. 134:S121-Abstract 693) and various other tumors. It is possible that the TIGIT/PVR interaction can shield such tumor cells from immune-mediated eradication by inhibiting anti-tumor responses of T and NK cells. Stanietsky et al. (2009) Proc. Nat'l Acad. Sci. (USA) 106: 17858 and Lozano et al. (2012) J. Immunol. 188:3869. Other experiments have identified a TIGIT$^+$ subset of regulatory T cells (T$_{regs}$) that selectively suppress Th1 and Th17 responses (Joller et al. (2014) Immunity 40:569), suggesting an alternative mechanism by which an anti-TIGIT antibody may enhance anti-tumor immune response.

TIGIT may act to "turn off" the immune response similarly to other co-inhibitory receptors such as CTLA-4, PD-1 and BTLA. Antibodies targeting CTLA-4 (ipilimumab) and PD-1 (nivolumab, pembrolizumab) have been approved for the treatment of human cancers, validating this therapeutic approach. Antibodies that bind to human TIGIT might also find use in treatment of cancers. See e.g. WO 2006/124667. In mouse models, antibody blockade of both PD-L1 and TIGIT leads to a synergistic enhancement of CD8$^+$ T cell mediated tumor rejection. Grogan et al. (2014) J. Immunol. 192(1) Suppl. 203.15; Johnston et al. (2014) Cancer Cell 26:1-15. Similar results have been obtained in animal models of melanoma. Inozume et al. (2014) J. Invest. Dermatol. 134:S121-Abstract 693. Some experiments suggest that TIGIT blockade is effective to enhance anti-tumor CD8$^+$ T cell response only in the presence of the co-activating receptor DNAM-1/CD226, which competes with TIGIT for binding to PVR/CD155. Johnston et al. (2014) Cancer Cell 26:1-15.

Amino acid sequences for various agonist anti-huTIGIT antibodies of the present invention are provided in the Sequence Listing, which is summarized at Table 2. For the reasons mentioned above, the C-terminal lysine is not included in any of sequences in the Sequence Listing for heavy chains or heavy chain constant domains. However, in an alternative embodiment, each heavy chain for the anti-huTIGIT antibodies of the present invention, and/or genetic construct encoding such antibodies or the heavy or light chains thereof, includes this additional lysine residue at the C-terminus of the heavy chain(s).

Additional anti-TIGIT mAbs that may be purified by the methods of the present invention may be found at WO 2017/053748, such as mAb 4.1D3 therein (variable domains at SEQ ID NOs: 34 and 36, with an IgG1 heavy chain constant domain). Other anti-TIGIT mAbs may be found at US 2009/0258013, such as mAb 10A7 therein (variable domains at SEQ ID NOs: 21 and 22, with an IgG1 heavy chain constant domain). Still other anti-TIGIT mAbs are found at WO 2017/059095, WO 2016/191643, WO 2017/037707, WO 2017/048824, and WO 2016/028656.

Other mAbs that May Find Use in Methods of the Present Invention

In other embodiments, the present invention provides improved methods for purifying antibodies, including therapeutic antibodies, that do not specifically bind to human TIGIT. Examples include the following antibodies, as disclosed in the following patents and publications.

An exemplary anti-PD-1 antibody is OPDIVO®/nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD-1 antibody is MK-3475 (KEYTRUDA®/pembrolizumab/formerly lambrolizumab) described in WO2012/145493; AMP-514/MEDI-0680 described in WO 2012/145493; and CT-011 (pidilizumab; previously CT-AcTibody or BAT; see, e.g., Rosenblatt et al. (2011) J. Immunotherapy 34:409). Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used.

In one embodiment, the anti-PD-L1 antibody is BMS-936559 (referred to as 12A4 in WO 2007/005874 and U.S. Pat. No. 7,943,743), MSB0010718C (WO2013/79174), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiment an anti-PD-L1 antibody is MEDI4736 (also known as Anti-B7-H1) or MPDL3280A (also known as RG7446). Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used.

In another aspect, the antibody is a GITR agonist. Suitable GITR antibodies include, for example, BMS-986153, BMS-986156, TRX-518 (WO 06/105021, WO 09/009116) and MK-4166 (WO 11/028683).

In certain embodiments, the anti-CTLA-4 antibody is an antibody selected from the group consisting of: YERVOY® (ipilimumab or antibody 10D1, described in PCT Publication WO 01/14424), tremelimumab (formerly ticilimumab, CP-675,206), and the anti-CTLA-4 antibody described in the following publications: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. Any of the anti-CTLA-4 antibodies disclosed in WO2013/173223 may also be used.

Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892 and WO2014/008218. In one embodiment, an anti-LAG-3 antibody is BMS-986016. Other art recognized anti-LAG-3 antibodies that can be used include IMP731 described in US 2011/007023. IMP-321 may also be used.

Antibody Manufacture

Antibodies of the present invention, including both specific antibodies for which sequences are provided and other, related anti-TIGIT antibodies, can be produced in a host cell transfectoma using, for example, a combination of recombinant DNA techniques and gene transfection methods as is well known in the art (Morrison, S. (1985) *Science* 229: 1202).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). Antibodies of the present invention can also be produced in glycoengineered strains of the yeast *Pichia pastoris*. Li et al. (2006) *Nat. Biotechnol.* 24:210.

Preferred mammalian host cells for expressing the recombinant antibodies described herein include Chinese Hamster Ovary (CHO cells) (including dhfr- CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bio-* eng. 97:544; Liu et al. (2011) *JBC* 28611211; Liu et al. (2011) *J. Biol. Chem.* 286:11211.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1

Non Reducing Capillary Electrophoresis Sodium Dodecyl Sulfate (CE-SDS)

To determine the percentage intact of mAb, samples were analyzed by capillary electrophoresis sodium dodecyl sulfate (CE-SDS). Under non-reducing conditions the antibody disulfide bonds were stabilized using iodoacetimide (IAM) to protect them from heat-induced partial reduction during the heat denaturation step. The sample was prepared in the presence of sodium dodecyl sulfate (SDS), an ionic detergent that coats unfolded proteins. The SDS masks the native charge of the protein providing a net negative charge which enables electrophoretic mobility separation based almost exclusively on size of the protein molecule(s). Electrophoretic separation was carried out by electrokinetic injection followed by applying a separation voltage to a bare fused silica capillary for forty minutes. Proteins were detected by absorbance at 220 nm. Corrected relative percent area (A % corr) is calculated and reported for each detected peak. This method was used to obtain the data presented in FIG. 2.

Example 2

Caliper LabChip® GX/GXII Microfluidic System Analysis

An alternative CE-SDS method described in Example 1 is use of the Caliper LabChip® GX/GXII Microfluidic system (Caliper LifeSciences, Waltham Mass., USA). This system is typically used for higher high throughput analysis of a large number of samples to perform non-reduced SDS-Polyacrylamide gel electrophoresis (PAGE) to determine if antibody is intact. Protein samples were diluted in buffer containing iodoacetamide (IAM) and SDS in a microtiter plate, and denatured by heat incubation. Reagents were pipetted onto the LabChip® GX II microfluidic chip and the chip was installed in the instrument. Each protein sample was aspirated onto the chip, mixed with fluorescent dye and electrophoretically separated. A separate destaining step was then performed on the chip. Optics within the instrument detected the fluorescent signal for each sample. The data were analyzed with the system software and the protein percent intact and concentration were determined.

Figure 5:
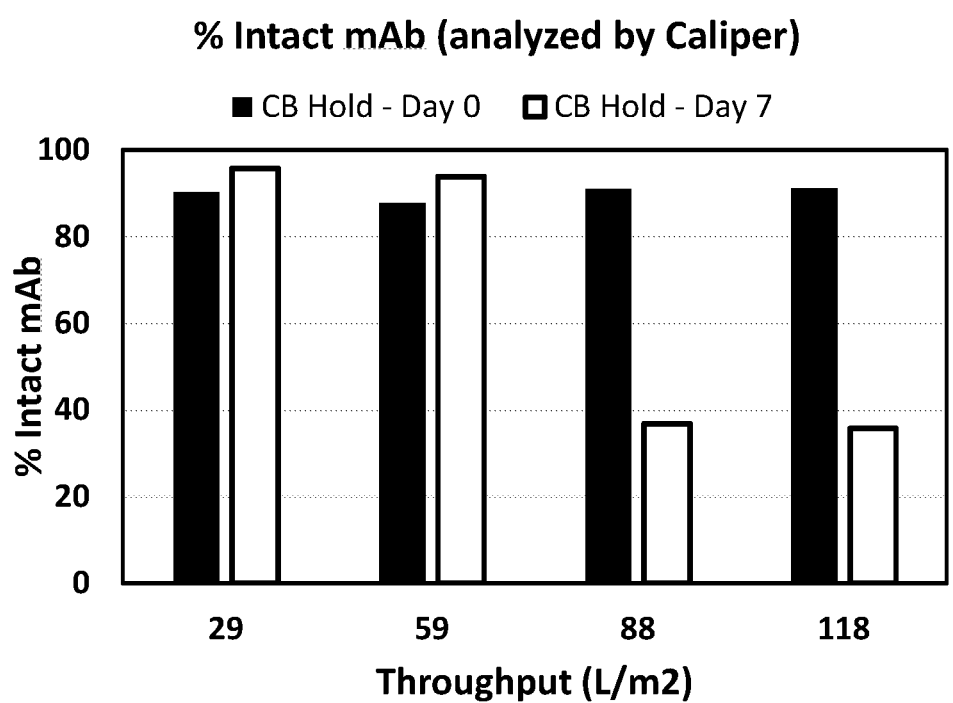
FIG. 5 shows percent intact mAb as a function of sample throughput during the depth filtration step. See Example 5. Percent intact mAb data are provided for samples immediately after depth filtration (solid bars) and after storage for 7 days without an air headspace (open bars). High throughput during depth filtration caused a significant reduction in intact mAb upon storage.

The Caliper LabChip® microfluidic analysis system was used to determine the percentage of intact mAb, as reported at FIGS. 3 and 5, and at Table 1. For FIG. 5 and Table 1, samples were pre-treated with the quenching agent 20 mM NEM (N-ethylmaleimide) to ensure the antibody remained in the reduced status for later measurements. The samples for FIG. 3, which were obtained from the GMP runs, were analyzed in a short time so the re-oxidation during sample storage was of less concern.

Example 3

Preventing Disulfide Bond Reduction by Air Overlay

Depth filtration of the cell culture harvest was performed to obtain clarified bulk (CB) antibody preparation (GMP #2, Batch 2). One quarter of the CB was subjected to protein A chromatography and viral inactivation the same day of filtration. The remaining CB was collected in three Disposable Clarified Harvest Bags, each of which was sealed with 20% air overlay. The Disposable Clarified Harvest Bags were stored at 20° C. with agitation using an impeller inside the bag. One of the Disposable Clarified Harvest Bags was then subjected to protein A chromatography and viral inactivation each successive day, or "cycle," until the entire CB had been purified. The resulting samples were referred to as CB Cycle 1 PAVIB, CB Cycle 2 PAVIB, CB Cycle 3 PAVIB, and CB Cycle 4 PAVIB. Percent intact mAb was determined for each sample using Caliper LabChip® microfluidic analysis, as described in Example 2. Separate experiments (GMP #1, Batch 1) was also performed using the same methods but without any air overlay or headspace of the present invention.

For the GMP #1 (Batch 1) samples, CB Cycle 1 PAVIB had >97% intact mAb but all other Cycles had <15% intact mAb. In contrast, all four Cycle samples for GMP #2 (Batch 2), including samples that had been stored up to nearly three days, showed >97% intact mAb. See FIG. 2A. Percent intact mAb for the pooled CB material (combining all cycles) prepared by a method of the present invention (Batch 2) was also determined after each subsequent downstream purification step, demonstrating that disulfide bond reduction did not occur at any point in the downstream process. See FIG. 3.

Example 4

Bench Scale Oxygenation Testing

Clarified harvest samples (Protein A Load) at 100% DO were obtained daily from manufacturing throughout the duration of the Protein A cycling (4 days). Upon receipt, samples were aseptically transferred to a 500 mL bottle and filled to the top, void of air. Samples were held in the development lab at ambient temperature (18-22° C.) until the last Protein A cycle was complete in manufacturing. Prior to purification, samples were measured for dissolved oxygen (DO) concentration by Nova Biomedical Stat Profile® pHOx. A portion of each sample was quenched with 20 mM NEM (N-ethylmaleimide) and purified using Protein A for Caliper LabChip® microfluidic analysis. The remaining sample was exposed to air and 'oxygenated' (aerated) for 4 hours using a stir plate to introduce air. The oxygenated samples were quenched with NEM and purified using Protein A for Caliper LabChip® microfluidic analysis. See Example 2 for Caliper LabChip® microfluidic analysis. Results are provided at Table 1.

Example 5

Effects of Throughput During Depth Filtration on Samples

Depth filtration of the cell culture harvest was performed on test scale to determine the effects of throughput. Samples were run through a 30SP02A dual layer depth filter (comprising an upstream filter with nominal pores size 10-1 μm and a downstream filter with nominal pores size 2-0.6 μm) or a 90ZB08A dual layer depth filter (comprising an upstream filter with nominal pores size 0.8-0.45 μm and a downstream filter with nominal pores size 0.65-0.2 μm) at a flux (LMH) of 100 L/m²/h and 200 L/m²/h, respectively. Zeta Plus™ Encapsulated System, 3M Purification Inc., Meriden Conn., USA. Differential pressure reading were taken for both depth filters at various throughput points. Results are provided at FIG. 4A. In addition, samples were taken at 30, 60, 90 and 120 L/m² for detection of LDH content and thiol content for the 30SP02A filtered samples. Results are provided at FIGS. 4B and 4C. Higher throughput correlated with high pressure build-up, high cell lysis (as measured by LDH content) and more reducing environment (as measured by thiol content).

In other experiments, samples were taken throughout the course of depth filtration at 29, 59, 88, and 118 L/m². A portion of each sample was analyzed for percentage intact mAb by Caliper LabChip® microfluidic analysis immediately. Another portion of each sample was staged in capped syringes without headspace, i.e. void of air. The prepared samples were held (static) at 20° C. for 7 days. Samples were quenched with 20 mM NEM and purified using Protein A for Caliper LabChip® microfluidic analysis. Results are provided at FIG. 5. Although all samples were initially nearly 90% intact mAb (solid bars), samples obtained at higher throughput (88 and 118 L/m²) exhibit <40% intact mAb after storage for 7 days (open bars), suggesting that high throughput should be avoided to prevent unwanted disulfide bond reduction during storage Example 6

Thiol Content as a Function of Oxygenation

Depth filtration was performed on cell culture harvest using a 10SP02A dual layer depth filter or a 30SP02A dual layer depth filter at benchtop scale. 10SP02A filters comprise an upstream filter with nominal pores size 10-1 μm and a downstream filter with nominal pores size 4-0.8 μm, and 30SP02A filters comprise an upstream filter with nominal pores size 10-1 μm and a downstream filter with nominal pores size 2-0.6 μm. Various flow rates (fluxes), such as 25, 50 and 75 LMH (liters/m²/hr) were evaluated to monitor the effect of flux and filter type on reduction to elucidate the effect of shear on cellular lysis. Thiol and LDH content were measured in end point filtration samples (filtration pool) and staged in capped syringes with and without headspace at 4° C. for 7 days. Samples without headspace were void of air. Samples with headspace had 20% headspace (v/v) as measured by the graduations on the syringe. Samples were quenched with 20 mM NEM and purified using Protein A for Caliper LabChip® microfluidic analysis. On day 7, the thiol content and residual oxygen content was directly measured using an Optical oxygen meter (Firesting O2, Pyroscience Sensor Technology GmbH, Aachen, Germany). Thiol content is presented as a function of % oxygen at FIG. 6.

TABLE 2

SUMMARY OF SEQUENCE LISTING

| SEQ ID NO. | Description |
| --- | --- |
| 1 | Human TIGIT polypeptide (NP_776160.2) |
| 2 | 15A6 VH domain |

TABLE 2-continued

SUMMARY OF SEQUENCE LISTING

| SEQ ID NO. | Description |
| --- | --- |
| 3 | 15A6 VH domain A72S |
| 4 | 15A6 VH domain N112T |
| 5 | 15A6 VH domain A72S N112T |
| 6 | 15A6 VL domain |
| 7 | 22G2 VH domain |
| 8 | 22G2 VH domain H3Q |
| 9 | 22G2 VL domain |
| 10 | 11G11 VH domain |
| 11 | 11G11 VL domain) |
| 12 | 10D7 VH domain |
| 13 | 10D7 VL domain |
| 14 | 15A6 CDRH1 |
| 15 | 15A6 CDRH2 |
| 16 | 15A6 CDRH3 |
| 17 | 15A6 CDRL1 |
| 18 | 15A6 CDRL2 |
| 19 | 15A6 CDRL3 |
| 20 | 22G2 CDRH1 |
| 21 | 22G2 CDRH2 |
| 22 | 22G2 CDRH3 |
| 23 | 22G2 CDRL1 |
| 24 | 22G2 CDRL2 |
| 25 | 22G2 CDRL3 |
| 26 | 11G11 CDRH1 |
| 27 | 11G11 CDRH2 |
| 28 | 11G11 CDRH3 |
| 29 | 11G11 CDRL1 |
| 30 | 11G11 CDRL2 |
| 31 | 11G11 CDRL3 |
| 32 | 10D7 CDRH1 |
| 33 | 10D7 CDRH2 |
| 34 | 10D7 CDRH3 |
| 35 | 10D7 CDRL1 |
| 36 | 10D7 CDRL2 |
| 37 | 10D7 CDRL3 |
| 38 | 22G2/15A6 epitope - huTIGIT residues 58-76 |
| 39 | 22G2 epitope - huTIGIT residues 107-117 |
| 40 | 11G11 epitope - huTIGIT residues 56-76 |
| 41 | 11G11 epitope - huTIGIT residues 111-114 |
| 42 | 11G11 epitope - huTIGIT residues 120-139 |
| 43 | 15A6 epitope - huTIGIT residues 132-139 |
| 44 | 22G2/11G11/15A6 core epitope - huTIGIT residues 65-76 |
| 45 | IgG1f constant domain (human) |
| 46 | IgG1 constant domain, allotypic variant (human) |
| 47 | IgG1. 3 constant domain (human) |
| 48 | IgG1.1f constant domain (human) |
| 49 | Kappa constant domain (human) |
| 50 | PVR/CD155 precursor alpha (human) NP_006496.4 |
| 51 | PVR/CD155 precursor beta (human) NP_001129240.1 |
| 52 | PVR/CD155 precursor gamma (human) NP_001129241.1 |
| 53 | PVR/CD155 precursor delta (human) NP_001129242.2 |

With regard to antibody sequences, the Sequence Listing provides the sequences of the mature variable regions of the heavy and light chains, i.e. the sequences do not include signal peptides.

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of minimizing disulfide bond reduction when purifying a monoclonal antibody (mAb) comprising;
   i) subjecting a cell culture of a cell line expressing the mAb to depth filtration to generate a partially clarified bulk antibody; and
   ii) storing a portion of the partially purified clarified bulk antibody for at least 12 hours in a disposable bag, comprising maintaining an air overlay in the disposable bag during storage, wherein the percentage of intact mAb does not drop below 90% at any point during storage.

2. The method of claim 1, wherein the air overlay comprises 5 to 50% of the interior volume of the disposable bag.

3. The method of claim 2, wherein the air overlay comprises approximately 20% of the interior volume of the disposable bag.

4. The method of claim 1 further comprising agitation of the partially purified clarified bulk antibody during storage.

5. The method of claim 4, wherein the percentage of intact mAb does not drop below 95% at any point during storage.

6. The method of claim 1, wherein the antibody is an anti-hu-T cell immunoreceptor with Ig and ITIM domains (TIGIT) antibody.

7. The method of claim 6, wherein the antibody comprises:
   a) CDRH1, CDRH2 and CDRH3 of SEQ ID NOs: 20, 21 and 22, respectively, and
   b) CDRL1, CDRL2 and CDRL3 of SEQ ID NOs: 23, 24 and 25, respectively.

8. The method of claim 7, wherein the antibody comprises:
   a) a heavy chain variable domain sequence of SEQ ID NO: 7 or 8, and
   b) a light chain variable domain sequence of SEQ ID NO: 9.

9. The method of claim 8, wherein the antibody comprises:
   a) a heavy chain sequence comprising SEQ ID NOs: 7 and 48, and
   b) a light chain sequence comprising SEQ ID NOs: 9 and 49.

10. The method of claim 8, wherein the antibody comprises:
    a) a heavy chain sequence comprising SEQ ID NOs: 8 and 48; and
    b) a light chain sequence comprising SEQ ID NOs: 9 and 49.

11. The method of claim 1 wherein the depth filtration is performed at a throughput of less than or equal to 80 L/m$^2$.

12. The method of claim 11 wherein the depth filtration is performed at a throughput of less than or equal to 70 L/m$^2$.

13. The method of claim 12 wherein the depth filtration is performed at a throughput of less than or equal to 60 L/m$^2$.

* * * * *

SEQUENCE LISTING

<160> NUMBER OF SEQ ID NOS: 53

<210> SEQ ID NO 1
<211> LENGTH: 244
<212> TYPE: PRT
<213> ORGANISM: Homo sapiens

<400> SEQUENCE: 1

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 2
<211> LENGTH: 118
<212> TYPE: PRT
<213> ORGANISM: Homo sapiens

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Ser Ser Ser Ala Trp Tyr Phe Asp Tyr Trp Gly Gln Gly Asn
                100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: human sequence with A72S modification

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Ser Ser Ser Ala Trp Tyr Phe Asp Tyr Trp Gly Gln Gly Asn
                100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: human sequence with N112Q modification

<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Ser Ser Ser Ala Trp Tyr Phe Asp Tyr Trp Gly Gln Gly Thr
                100                 105                 110

Leu Val Thr Val Ser Ser
        115

-continued

```
<210> SEQ ID NO 5
<211> LENGTH: 118
<212> TYPE: PRT
<213> ORGANISM: Artificial Sequence
<220> FEATURE:
<223> OTHER INFORMATION: human sequence with A72S and N112T
      modifications

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Ser Ser Ala Trp Tyr Phe Asp Tyr Trp Gly Gln Gly Thr
            100                 105                 110

Leu Val Thr Val Ser Ser
        115

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Tyr
                85                  90                  95

Thr Phe Gly Gln Gly Thr Lys Leu Glu Ile Lys
            100                 105

<210> SEQ ID NO 7
<211> LENGTH: 130
<212> TYPE: PRT
<213> ORGANISM: Homo sapiens

<400> SEQUENCE: 7

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45
```

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Val Ser Gly Asn Tyr Tyr Asn Val Asp Tyr
                100                 105                 110

Tyr Phe Phe Gly Val Asp Val Trp Gly Gln Gly Thr Thr Val Thr Val
            115                 120                 125

Ser Ser
    130

<210> SEQ ID NO 8
<211> LENGTH: 130
<212> TYPE: PRT
<213> ORGANISM: Artificial Sequence
<220> FEATURE:
<223> OTHER INFORMATION: human sequence with H3Q modification

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ile Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Val Ser Gly Asn Tyr Tyr Asn Val Asp Tyr
                100                 105                 110

Tyr Phe Phe Gly Val Asp Val Trp Gly Gln Gly Thr Thr Val Thr Val
            115                 120                 125

Ser Ser
    130

<210> SEQ ID NO 9
<211> LENGTH: 109
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Pro
            85                  90                  95

Leu Phe Thr Phe Gly Pro Gly Thr Lys Val Asp Ile Lys
            100                 105
```

<210> SEQ ID NO 10
<211> LENGTH: 126
<212> TYPE: PRT
<213> ORGANISM: Homo sapiens

<400> SEQUENCE: 10

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser His Tyr Trp Gly Trp Ile Arg Gln Pro Pro Gly Lys Gly Leu Glu
        35                  40                  45

Trp Ile Gly Asn Ile Phe Tyr Ser Gly His Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gly Leu Leu Trp Phe Gly Gly Leu Ser Pro Tyr Tyr
            100                 105                 110

Phe Asp Tyr Trp Gly Gln Gly Thr Leu Val Thr Val Ser Ser
        115                 120                 125
```

<210> SEQ ID NO 11
<211> LENGTH: 106
<212> TYPE: PRT
<213> ORGANISM: Homo sapiens

<400> SEQUENCE: 11

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Leu Glu Ile Lys
            100                 105
```

<210> SEQ ID NO 12
<211> LENGTH: 128
<212> TYPE: PRT
<213> ORGANISM: Homo sapiens

<400> SEQUENCE: 12

```
Gln Gly Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Asn Tyr
```

```
                    20                  25                  30

Ala Ile Ser Trp Val Arg Gln Ala Pro Gly Gln Gly Leu Glu Trp Met
             35                  40                  45

Gly Gly Ile Ile Pro Phe Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ala Ala Ala Gly Thr Thr Arg Tyr Gly Tyr Tyr Tyr
             100                 105                 110

Tyr Gly Met Asp Val Trp Gly Gln Gly Thr Thr Val Thr Val Ser Ser
         115                 120                 125

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Ile
                 85                  90                  95

Thr Phe Gly Gln Gly Thr Arg Leu Glu Ile Lys
            100                 105

<210> SEQ ID NO 14
<211> LENGTH: 7
<212> TYPE: PRT
<213> ORGANISM: Homo sapiens

<400> SEQUENCE: 14

Ser Ser Arg Tyr Phe Trp Gly
 1               5

<210> SEQ ID NO 15
<211> LENGTH: 16
<212> TYPE: PRT
<213> ORGANISM: Homo sapiens

<400> SEQUENCE: 15

Tyr Ile Tyr Tyr Arg Gly Ser Thr Tyr Tyr Asn Pro Ser Leu Lys Ser
 1               5                  10                  15

<210> SEQ ID NO 16
<211> LENGTH: 8
<212> TYPE: PRT
<213> ORGANISM: Homo sapiens

<400> SEQUENCE: 16
```

Ser Ser Ala Trp Tyr Phe Asp Tyr
1               5

<210> SEQ ID NO 17
<211> LENGTH: 12
<212> TYPE: PRT
<213> ORGANISM: Homo sapiens

<400> SEQUENCE: 17

Arg Ala Ser Gln Ser Val Ser Ser Ser Tyr Leu Ala
1               5                   10

<210> SEQ ID NO 18
<211> LENGTH: 7
<212> TYPE: PRT
<213> ORGANISM: Homo sapiens

<400> SEQUENCE: 18

Gly Ala Ser Ser Arg Ala Thr
1               5

<210> SEQ ID NO 19
<211> LENGTH: 8
<212> TYPE: PRT
<213> ORGANISM: Homo sapiens

<400> SEQUENCE: 19

Gln Gln Tyr Gly Ser Leu Tyr Thr
1               5

<210> SEQ ID NO 20
<211> LENGTH: 7
<212> TYPE: PRT
<213> ORGANISM: Homo sapiens

<400> SEQUENCE: 20

Ser Gly Ile Tyr Tyr Trp Ser
1               5

<210> SEQ ID NO 21
<211> LENGTH: 16
<212> TYPE: PRT
<213> ORGANISM: Homo sapiens

<400> SEQUENCE: 21

Tyr Ile Tyr Tyr Ser Gly Ser Thr Asn Tyr Asn Pro Ser Leu Lys Ser
1               5                   10                  15

<210> SEQ ID NO 22
<211> LENGTH: 20
<212> TYPE: PRT
<213> ORGANISM: Homo sapiens

<400> SEQUENCE: 22

Asp Tyr Tyr Val Ser Gly Asn Tyr Asn Val Asp Tyr Tyr Phe Phe
1               5                   10                  15

Gly Val Asp Val
                20

<210> SEQ ID NO 23
<211> LENGTH: 11
<212> TYPE: PRT
<213> ORGANISM: Homo sapiens

<400> SEQUENCE: 23

Arg Ala Ser Gln Ser Val Ser Ser Tyr Leu Ala
1               5                   10

<210> SEQ ID NO 24
<211> LENGTH: 7
<212> TYPE: PRT
<213> ORGANISM: Homo sapiens

<400> SEQUENCE: 24

Asp Ala Ser Asn Arg Ala Thr
1               5

<210> SEQ ID NO 25
<211> LENGTH: 11
<212> TYPE: PRT
<213> ORGANISM: Homo sapiens

<400> SEQUENCE: 25

Gln Gln Arg Ser Asn Trp Pro Pro Leu Phe Thr
1               5                   10

<210> SEQ ID NO 26
<211> LENGTH: 7
<212> TYPE: PRT
<213> ORGANISM: Homo sapiens

<400> SEQUENCE: 26

Ser Ser Ser His Tyr Trp Gly
1               5

<210> SEQ ID NO 27
<211> LENGTH: 16
<212> TYPE: PRT
<213> ORGANISM: Homo sapiens

<400> SEQUENCE: 27

Asn Ile Phe Tyr Ser Gly His Thr Tyr Tyr Asn Pro Ser Leu Lys Ser
1               5                   10                  15

<210> SEQ ID NO 28
<211> LENGTH: 16
<212> TYPE: PRT
<213> ORGANISM: Homo sapiens

<400> SEQUENCE: 28

Gln Gly Leu Leu Trp Phe Gly Gly Leu Ser Pro Tyr Tyr Phe Asp Tyr
1               5                   10                  15

<210> SEQ ID NO 29
<211> LENGTH: 11
<212> TYPE: PRT
<213> ORGANISM: Homo sapiens

<400> SEQUENCE: 29

Arg Ala Ser Gln Ser Val Ser Ser Tyr Leu Ala
1               5                   10

<210> SEQ ID NO 30
<211> LENGTH: 7
<212> TYPE: PRT
<213> ORGANISM: Homo sapiens

<400> SEQUENCE: 30

Asp Ala Ser Asn Arg Ala Thr

```
1               5

<210> SEQ ID NO 31
<211> LENGTH: 8
<212> TYPE: PRT
<213> ORGANISM: Homo sapiens

<400> SEQUENCE: 31

Gln Gln Arg Ser Asn Trp Pro Thr
1               5

<210> SEQ ID NO 32
<211> LENGTH: 5
<212> TYPE: PRT
<213> ORGANISM: Homo sapiens

<400> SEQUENCE: 32

Asn Tyr Ala Ile Ser
1               5

<210> SEQ ID NO 33
<211> LENGTH: 17
<212> TYPE: PRT
<213> ORGANISM: Homo sapiens

<400> SEQUENCE: 33

Gly Ile Ile Pro Phe Phe Gly Thr Ala Asn Tyr Ala Gln Lys Phe Gln
1               5                   10                  15

Gly

<210> SEQ ID NO 34
<211> LENGTH: 19
<212> TYPE: PRT
<213> ORGANISM: Homo sapiens

<400> SEQUENCE: 34

Gly Gly Ala Ala Ala Gly Thr Thr Arg Tyr Gly Tyr Tyr Tyr Tyr Gly
1               5                   10                  15

Met Asp Val

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Trp Leu Ala
1               5                   10

<210> SEQ ID NO 36
<211> LENGTH: 7
<212> TYPE: PRT
<213> ORGANISM: Homo sapiens

<400> SEQUENCE: 36

Ala Ala Ser Ser Leu Gln Ser
1               5

<210> SEQ ID NO 37
<211> LENGTH: 9
<212> TYPE: PRT
<213> ORGANISM: Homo sapiens

<400> SEQUENCE: 37
```

```
Gln Gln Tyr Asn Ser Tyr Pro Ile Thr
1               5
```

<210> SEQ ID NO 38
<211> LENGTH: 19
<212> TYPE: PRT
<213> ORGANISM: Homo sapiens

<400> SEQUENCE: 38

```
Asn Trp Glu Gln Gln Asp Gln Leu Leu Ala Ile Cys Asn Ala Asp Leu
1               5                   10                  15

Gly Trp His
```

<210> SEQ ID NO 39
<211> LENGTH: 11
<212> TYPE: PRT
<213> ORGANISM: Homo sapiens

<400> SEQUENCE: 39

```
Phe Cys Ile Tyr His Thr Tyr Pro Asp Gly Thr
1               5                   10
```

<210> SEQ ID NO 40
<211> LENGTH: 21
<212> TYPE: PRT
<213> ORGANISM: Homo sapiens

<400> SEQUENCE: 40

```
Gln Val Asn Trp Glu Gln Gln Asp Gln Leu Leu Ala Ile Cys Asn Ala
1               5                   10                  15

Asp Leu Gly Trp His
            20
```

<210> SEQ ID NO 41
<211> LENGTH: 4
<212> TYPE: PRT
<213> ORGANISM: Homo sapiens

<400> SEQUENCE: 41

```
His Thr Tyr Pro
1
```

<210> SEQ ID NO 42
<211> LENGTH: 20
<212> TYPE: PRT
<213> ORGANISM: Homo sapiens

<400> SEQUENCE: 42

```
Gly Arg Ile Phe Leu Glu Val Leu Glu Ser Ser Val Ala Glu His Gly
1               5                   10                  15

Ala Arg Phe Gln
            20
```

<210> SEQ ID NO 43
<211> LENGTH: 8
<212> TYPE: PRT
<213> ORGANISM: Homo sapiens

<400> SEQUENCE: 43

```
Ala Glu His Gly Ala Arg Phe Gln
1               5
```

```
<210> SEQ ID NO 44
<211> LENGTH: 12
<212> TYPE: PRT
<213> ORGANISM: Homo sapiens

<400> SEQUENCE: 44

Leu Leu Ala Ile Cys Asn Ala Asp Leu Gly Trp His
1               5                   10

<210> SEQ ID NO 45
<211> LENGTH: 329
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 46
<211> LENGTH: 329
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 47
<211> LENGTH: 329
<212> TYPE: PRT
<213> ORGANISM: Homo sapiens

<400> SEQUENCE: 47

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 48
<211> LENGTH: 329
<212> TYPE: PRT
<213> ORGANISM: Homo sapiens

<400> SEQUENCE: 48

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 49
<211> LENGTH: 107
<212> TYPE: PRT
<213> ORGANISM: Homo sapiens

<400> SEQUENCE: 49

Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 417
<212> TYPE: PRT
<213> ORGANISM: Homo sapiens
<220> FEATURE:
<221> NAME/KEY: SIGNAL
<222> LOCATION: (1)..(20)

<400> SEQUENCE: 50

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
                20                  25                  30

Ala Pro Thr Gln Val Pro Gly Phe Leu Gly Asp Ser Val Thr Leu Pro
                35                  40                  45

Cys Tyr Leu Gln Val Pro Asn Met Glu Val Thr His Val Ser Gln Leu
50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
                100                 105                 110

Leu Arg Val Glu Asp Glu Gly Asn Tyr Thr Cys Leu Phe Val Thr Phe
                115                 120                 125

Pro Gln Gly Ser Arg Ser Val Asp Ile Trp Leu Arg Val Leu Ala Lys
                130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
                195                 200                 205

Val Pro Ser Ser Gln Val Asp Gly Lys Asn Val Thr Cys Lys Val Glu
                210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
                260                 265                 270

Glu Pro Thr Gly Tyr Asn Trp Ser Thr Thr Met Gly Pro Leu Pro Pro
                275                 280                 285

Phe Ala Val Ala Gln Gly Ala Gln Leu Leu Ile Arg Pro Val Asp Lys
                290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
```

```
                    325                 330                 335
His Ser Gly Met Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
                355                 360                 365

Lys Cys Ser Arg Glu Val Leu Trp His Cys His Leu Cys Pro Ser Ser
                370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg

<210> SEQ ID NO 51
<211> LENGTH: 372
<212> TYPE: PRT
<213> ORGANISM: Homo sapiens
<220> FEATURE:
<221> NAME/KEY: SIGNAL
<222> LOCATION: (1)..(27)

<400> SEQUENCE: 51

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
                20                  25                  30

Ala Pro Thr Gln Val Pro Gly Phe Leu Gly Asp Ser Val Thr Leu Pro
                35                  40                  45

Cys Tyr Leu Gln Val Pro Asn Met Glu Val Thr His Val Ser Gln Leu
            50                  55                  60

Thr Trp Ala Arg His Gly Glu Ser Gly Ser Met Ala Val Phe His Gln
65              70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
                100                 105                 110

Leu Arg Val Glu Asp Glu Gly Asn Tyr Thr Cys Leu Phe Val Thr Phe
                115                 120                 125

Pro Gln Gly Ser Arg Ser Val Asp Ile Trp Leu Arg Val Leu Ala Lys
            130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
                195                 200                 205

Val Pro Ser Ser Gln Val Asp Gly Lys Asn Val Thr Cys Lys Val Glu
            210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
```

```
              260                 265                 270
Glu Pro Thr Gly Tyr Asn Trp Ser Thr Thr Met Gly Pro Leu Pro Pro
            275                 280                 285

Phe Ala Val Ala Gln Gly Ala Gln Leu Leu Ile Arg Pro Val Asp Lys
            290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Thr Glu His Ala Ser Ala Ser Ala Asn Gly His Val Ser
                340                 345                 350

Tyr Ser Ala Val Ser Arg Glu Asn Ser Ser Ser Gln Asp Pro Gln Thr
            355                 360                 365

Glu Gly Thr Arg
    370

<210> SEQ ID NO 52
<211> LENGTH: 364
<212> TYPE: PRT
<213> ORGANISM: Homo sapiens
<220> FEATURE:
<221> NAME/KEY: SIGNAL
<222> LOCATION: (1)..(27)

<400> SEQUENCE: 52

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
                20                  25                  30

Ala Pro Thr Gln Val Pro Gly Phe Leu Gly Asp Ser Val Thr Leu Pro
            35                  40                  45

Cys Tyr Leu Gln Val Pro Asn Met Glu Val Thr His Val Ser Gln Leu
50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
210                 215                 220

His Glu Ser Phe Glu Lys Pro Gln Leu Leu Thr Val Asn Leu Thr Val
225                 230                 235                 240
```

```
Tyr Tyr Pro Pro Glu Val Ser Ile Ser Gly Tyr Asp Asn Asn Trp Tyr
            245                 250                 255

Leu Gly Gln Asn Glu Ala Thr Leu Thr Cys Asp Ala Arg Ser Asn Pro
        260                 265                 270

Glu Pro Thr Gly Tyr Asn Trp Ser Thr Thr Met Gly Pro Leu Pro Pro
    275                 280                 285

Phe Ala Val Ala Gln Gly Ala Gln Leu Leu Ile Arg Pro Val Asp Lys
290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Gly Thr Glu His Ala Ser
                325                 330                 335

Ala Ser Ala Asn Gly His Val Ser Tyr Ser Ala Val Ser Arg Glu Asn
            340                 345                 350

Ser Ser Ser Gln Asp Pro Gln Thr Glu Gly Thr Arg
        355                 360
```

<210> SEQ ID NO 53
<211> LENGTH: 392
<212> TYPE: PRT
<213> ORGANISM: Homo sapiens
<220> FEATURE:
<221> NAME/KEY: SIGNAL
<222> LOCATION: (1)..(27)

<400> SEQUENCE: 53

```
Met Ala Arg Ala Met Ala Ala Trp Pro Leu Leu Leu Val Ala Leu Leu
1               5                   10                  15

Leu Val Leu Ser Trp Pro Pro Gly Thr Gly Asp Val Val Val Gln
        20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240
```

-continued

```
Tyr Tyr Pro Pro Glu Val Ser Ile Ser Gly Tyr Asp Asn Asn Trp Tyr
            245                 250                 255

Leu Gly Gln Asn Glu Ala Thr Leu Thr Cys Asp Ala Arg Ser Asn Pro
        260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
        290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
            355                 360                 365

Lys Cys Ser Arg Glu Val Leu Trp His Cys His Leu Cys Pro Ser Ser
        370                 375                 380

Glu His His Gln Ser Cys Arg Asn
385                 390
```